(12) United States Patent
Delfosse et al.

(10) Patent No.: US 11,033,379 B2
(45) Date of Patent: *Jun. 15, 2021

(54) IMPLANTABLE SYSTEM WITH ELASTIC COMPONENTS

(71) Applicant: Mathys AG Bettlach, Bettlach (CH)

(72) Inventors: Daniel Delfosse, Jegenstorf (CH); Alessandro De Cesaris, Derendinger (CH); Clemens Dransfeld, Kreuzlingen (CH); Christian Rytka, Wehr (DE)

(73) Assignee: Mathys AG Bettlach, Bettlach (CH)

( * ) Notice: Subject to any disclaimer, the term of this patent is extended or adjusted under 35 U.S.C. 154(b) by 247 days.

This patent is subject to a terminal disclaimer.

(21) Appl. No.: 15/955,298

(22) Filed: Apr. 17, 2018

(65) Prior Publication Data

US 2018/0228595 A1 Aug. 16, 2018

Related U.S. Application Data

(62) Division of application No. 14/358,626, filed as application No. PCT/EP2012/072676 on Nov. 15, 2012, now Pat. No. 9,993,333.

(30) Foreign Application Priority Data

Nov. 30, 2011 (DE) ...................... 10 2011 087 404.6

(51) Int. Cl.
*A61F 2/08* (2006.01)
*A61B 17/04* (2006.01)
*A61B 17/00* (2006.01)

(52) U.S. Cl.
CPC ............ *A61F 2/08* (2013.01); *A61B 17/0401* (2013.01); *A61F 2/0811* (2013.01);
(Continued)

(58) Field of Classification Search
CPC ..... A61B 2017/0046; A61F 2002/0841; A61F 2002/0864
See application file for complete search history.

(56) References Cited

U.S. PATENT DOCUMENTS 4,610,688 A * 9/1986 Silvestrini ................ A61F 2/06
623/1.53
9,993,333 B2 * 6/2018 Delfosse .................... A61F 2/08
(Continued)

FOREIGN PATENT DOCUMENTS

WO    WO-2010124760 A1 * 11/2010    ............ A61F 2/0811

OTHER PUBLICATIONS

Translation of WO2010124760 retrieved from espacenet on Apr. 24, 2020. (Year: 2020).*

*Primary Examiner* — Megan Y Wolf
(74) *Attorney, Agent, or Firm* — Kenneth E. Horton; Kirton McConkie

(57) ABSTRACT

A system (100) for a controlled stressing of a reconstructed or re-natured ligament of a human or animal body comprises an anchoring element (10) for implantation in a first bone (50), at least one connecting element (120) and a holding element (30), which fixes the at least one connecting element (20) in a second bone. According to the invention, an elastomer element (125) is arranged in the anchoring element and/or in the connecting element (120) and provides a defined elastic action through the cooperation of elastomer element (125) with the connecting element (120).

14 Claims, 7 Drawing Sheets

Figure 1:
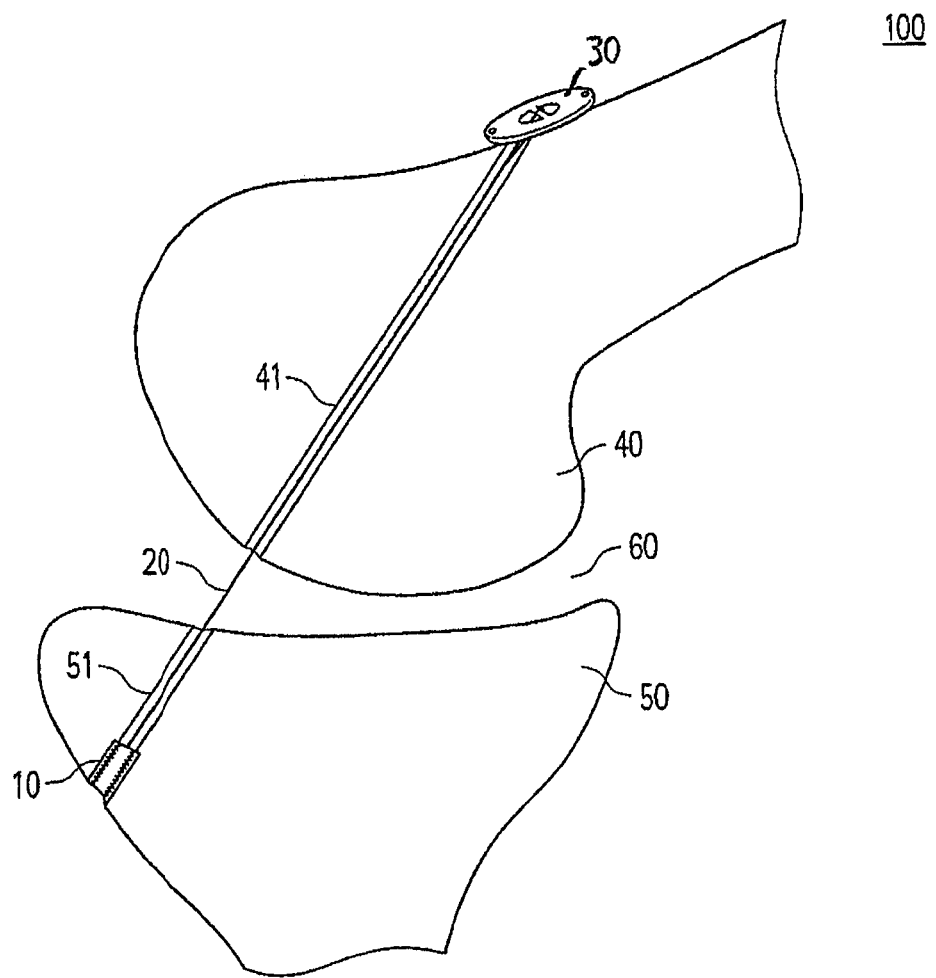

(52) U.S. Cl.
CPC .............. *A61B 2017/00862* (2013.01); *A61B 2017/0403* (2013.01); *A61B 2017/044* (2013.01); *A61B 2017/0445* (2013.01); *A61B 2017/0446* (2013.01); *A61B 2017/0451* (2013.01); *A61B 2017/0453* (2013.01); *A61B 2017/0454* (2013.01); *A61B 2017/0462* (2013.01); *A61F 2002/0823* (2013.01); *A61F 2002/0835* (2013.01); *A61F 2002/0841* (2013.01); *A61F 2002/0847* (2013.01); *A61F 2002/0864* (2013.01); *A61F 2002/0882* (2013.01); *A61F 2210/0004* (2013.01); *A61F 2210/0057* (2013.01); *A61F 2210/0066* (2013.01); *A61F 2220/0016* (2013.01); *A61F 2220/0033* (2013.01); *A61F 2230/0006* (2013.01); *A61F 2230/0023* (2013.01); *A61F 2230/0067* (2013.01); *A61F 2250/0007* (2013.01); *A61F 2250/0012* (2013.01); *A61F 2250/0017* (2013.01); *A61F 2250/0018* (2013.01)

(56) References Cited

U.S. PATENT DOCUMENTS

| | | | | |
|---|---|---|---|---|
| 2005/0251260 A1* | 11/2005 | Gerber | ............... | A61F 2/4425 623/17.13 |
| 2011/0046733 A1* | 2/2011 | Eggli | ............... | A61B 17/68 623/13.14 |
| 2011/0106265 A1* | 5/2011 | Wolfson | ............... | A61F 2/0811 623/18.11 |

\* cited by examiner

IMPLANTABLE SYSTEM WITH ELASTIC COMPONENTS

CROSS-REFERENCE TO RELATED APPLICATION

This patent application is a divisional application of U.S. Pat. No. 9,993,333 filed on May 15, 2014, the entire disclosure of which is hereby incorporated by reference.

The invention relates to an implantable system with elastic components for the controlled stressing of a reconstructed or re-natured ligament of a human or animal body.

The human knee joint is stabilised by the front cruciate ligament and the rear cruciate ligament in the interior of the knee joint. In the case of a twisting trauma of the knee joint, these two ligaments, especially the front cruciate ligament are overloaded, and a rupture respectively a detachment of the ligament occurs as a result. If conservative therapy approaches or attempts to stitch the front cruciate ligament do not lead to a stabilisation of the injured knee joint, the front cruciate ligament is often removed and the knee-joint stability is restored by a transplant made of tendon material or synthetic ligament. In this context, the damaged natural ligament is completely removed from the knee joint. However, the artificial replacement ligament can take over its function only inadequately. In particular, sensitivity is completely lost, which leads to an overloading and therefore to an increased wear on the artificial prosthetic ligament.

This fact and the self-healing tendency of every ligament of the human body is exploited by a system described in WO 2010/124760 A1 for the controlled stressing of a reconstructed or re-natured ligament. In this context, during the healing phase, a connecting element is attached by an anchoring respectively holding element to the two bones to be connected, which ensures a relief of the natural ligament and therefore allows the ligament to grow together naturally. The anchoring element provides a cushioning device in order to guarantee a uniform tensile stress within the system and to allow the flexing of the treated knee. After the healing of the natural ligament, the implantable system has fulfilled its task and is no longer required. WO 2010/124760 A1 discloses that one or more components of the system comprise a bio-absorbable material and dissolve of their own accord.

In particular, components of such an implantable system which comprise metallic material are described by patients as disturbing and painful and must therefore be removed operatively or arthroscopically after the healing of the ligament. Such an intervention is associated with risks and discomfort for the patient and generates additional costs.

The object of the present invention is therefore to construct as many components as possible of the implantable system from a material which is well tolerated by the human body and hardly leads to irritations or pain when retained within the patient. In this context, the implantable system should provide an elasticity similar to the elasticity characteristic of the natural ligament.

The object is achieved by the system according to the invention as specified in claim 1. In the dependent claims, advantageous further developments of the system according to the invention are specified.

The system according to the invention for a controlled stressing of a reconstructed or re-natured ligament of a human or animal body comprises an anchoring element for implantation in a first bone, at least one connecting element and a holding element which fixes the at least one connecting element in a second bone. According to the invention, an elastomer element is arranged in the anchoring element and/or in the connecting element and provides a defined elastic action through the cooperation of elastomer element with the anchoring element respectively the connecting element.

Through the selection and composition of the materials of the elastomer element, elastic moduli can be realised over a wide range. Through the cooperation of the elastomer element with the anchoring element and the connecting element, an elasticity characteristic of the system similar to that of a natural ligament can be achieved with favourable material and structural combinations. Furthermore, many elastomers are bio-compatible, so that they have no damaging effect on human or animal tissue. As a result of their deformability, they have a considerably less irritating effect and can therefore also remain in the body after the healing of the ligament.

The elastomer element is advantageously made of polyethylene and/or polyester and/or polyurethane and/or silicon. In the case of a use in the human body, the named materials have bio-compatible properties and also provide a favourable elastic behaviour.

With a cooperation of the elastomer element with a connecting element, it is advantageous if the elastomer element provides a smaller elastic modulus than the connecting element. Accordingly, in the case of a low tensile stress on the connecting element, the elastic modulus of the elastomer predominates, and in the case of a strong tensile stress, the significantly larger elastic modulus of the material of the connecting element predominates. Accordingly, the strain characteristic of the connecting element in interaction with the elastomer element corresponds to the strain characteristic of a natural ligament.

It is particularly advantageous if the connecting element is plaited and/or knitted spun and/or twisted and/or woven, and every first individual fibre enclose an angle $\tau$ between 5° and 85° relative to the longitudinal axis of the connecting element. As a result, the connecting element achieves the possibility of being elongated in the axial direction and achieving an elastic action, even if the individual fibres themselves are made from a non-elastic or only very slightly elastic material.

The connecting element is advantageously embodied in a tubular shape, and the elastomer element is arranged within a portion of the axial cavity of the tubular connecting element. The course of the elasticity curve, also referred to as the strain characteristic, of such a combination provides a progressive course, because the cross-section under compression and the local stress concentration, also referred to as the shape factor, increase as a result of the large deformation. Additionally, the progressive course of the strain characteristic is influenced by the angle with which the individual fibres of the connecting element are woven, plaited, spun, twisted and/or knitted relative to the longitudinal axis of the same. With an increasing tensile stress, the elasticity characteristic of the elastomer element, which is determined by the pressure of the tubular connecting element on the elastomer element in the radial direction, initially predominates. At the same time, the individual fibres of the connecting element are aligned from an angle $\tau$ relative to the longitudinal axis without tensile stress to an angle of approximately 0° relative to the longitudinal axis with strong tensile stress. The combination of connecting element and elastomer element can stretch no further and the elasticity declines strongly.

A connecting element in which the elastomer is embodied as a plurality of second individual fibres and is spun and/or knitted and/or woven and/or twisted and/or plaited with a plurality of first individual fibres to form a connecting element provides a similar strain characteristic. It is advantageous if the individual fibres contain a polymer, especially polyethylene and/or polyester, and the connecting element is formed from a plurality of individual fibres, especially made from polyethylene and/or polyester. The named polymers provide a relatively high elastic modulus, so that after a stretching of the woven fibre material, the elasticity of the combination is strongly increased. Furthermore, these polymers are bio-compatible and therefore suitable for implantation in the body.

It is also advantageous if an elastomer element is arranged as a cushioning device in the interior of an outer element of the anchoring element between a contact surface of the outer element and a sleeve. In this context, the connecting element is fixed in the sleeve and guided out of the anchoring element through an opening in the contact surface of the outer element. The elastomer element thus takes over the task of a cushioning element and can, for example, replace an arrangement of metallic springs.

In this context, it is advantageous if the sleeve is mounted in a displaceable manner in the outer element. In the event of a tensile stress on the connecting element, the sleeve itself is pressed by the displaceable sleeve against the elastomer element, which itself rigidly mounted through contact against the anchoring element, and leads to a compression of the elastomer element.

In this context, it is particularly advantageous if the connecting element is arranged in an axial recess in the elastomer element. When the elastomer element is compressed, the elastomer element also expands in the axial direction and, in this context, clamps in the connecting element. This represents a further strong increase of the elastic modulus of the combination of anchoring element and elastomer element.

It is also advantageous, if the connecting element is guided around the periphery of the elastomer element in a screw shape respectively spiral shape. In the case of a tensile stress of the connecting element, a radially inwardly directed force acts on the periphery of the elastomer element and presses the latter together. Accordingly, the rigidity of the elastomer element achieves a cushioned elongation of the implantable system. Here also, the compressibility of the elastomer element decreases with increasing constriction, and the elastic modulus rises with increasing compression. If the sleeve is arranged in a displaceable manner within the connecting element, a compression in the axial direction has an additional effect.

It is also advantageous if the sleeve is fixed to the outer element in an immovable manner, especially if the spring curve of the system is not to be influenced by an additional axial compression.

It is further advantageous if the elastomer element provides peripheral grooves which do not extend parallel to the longitudinal axis of the elastomer element, and the connecting element is guided in these grooves. These grooves prevent the connecting element from slipping out and guarantee a controlled pressure-application point on the elastomer element. Furthermore, such an arrangement simplifies the assembly of the anchoring element respectively the threading of the thread through the anchoring element.

An elastomer element which is formed from a plurality of tongue-shaped protrusions is also advantageous, whereas the protrusions are directed inwardly in alternation on opposite sides of the interior of the outer element of the anchoring element and attached in a radially overlapping manner. In this context, the connecting element is guided in the intermediate space between the protrusions. In the case of a tensile stress on the connecting element, the tongue-shaped protrusions of the elastomer element are deformed in the direction of the tensile force. With an increasing deformation of the protrusions, the spacing distance between the protrusions is reduced and the thread is clamped between the protrusions. This achieves a considerable increase in the elastic modulus.

It is advantageous if the elastomer element provides a cylindrical shape. The elastic modulus and the compressibility of the elastomer element are strongly dependent upon the shape of the elastomer element. The cylindrical shape allows a uniform, radially inwardly acting transfer of force. However, the cylindrical shape also allows a good transmission of force in the axial direction.

Figure 2:
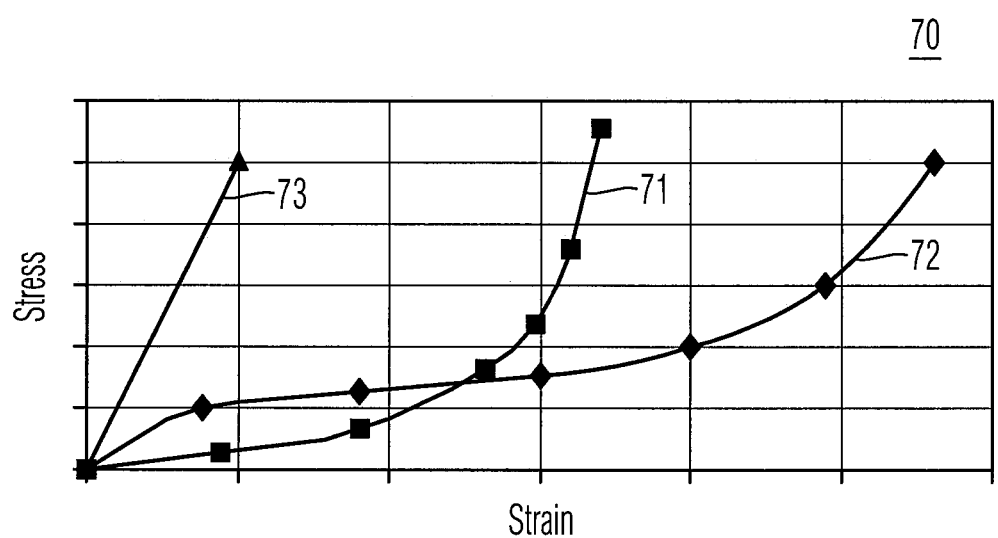
Figure 3A:
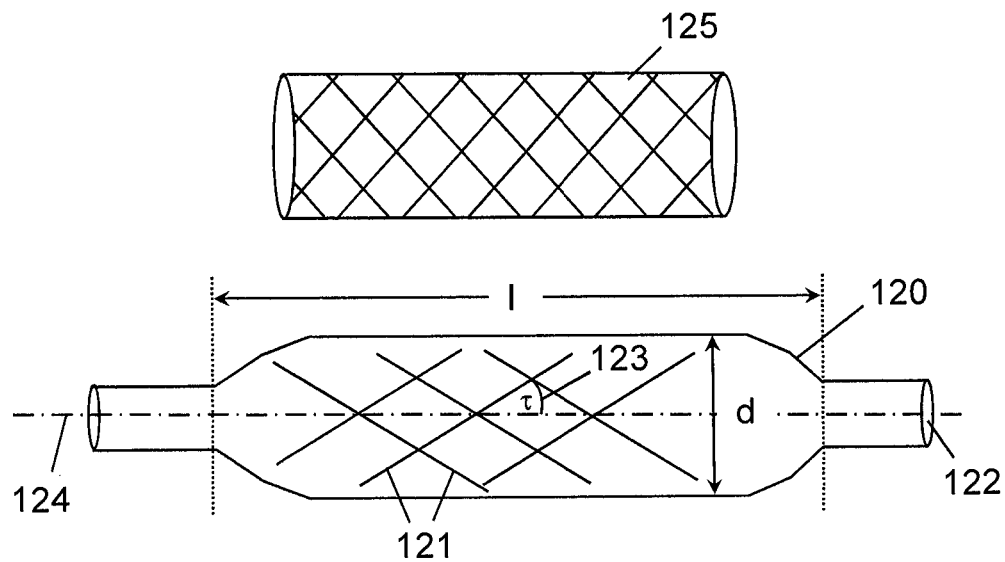
Figure 3B:
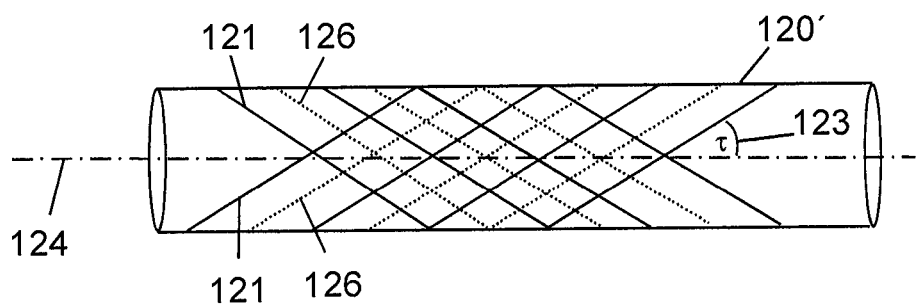
Figure 4:
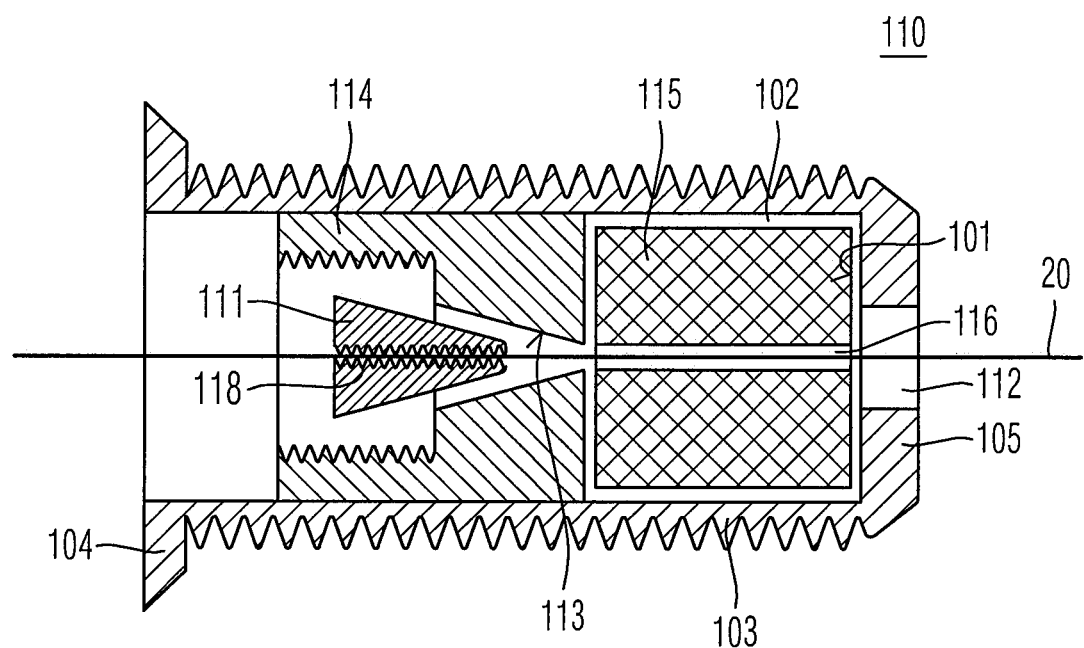
Figure 5:
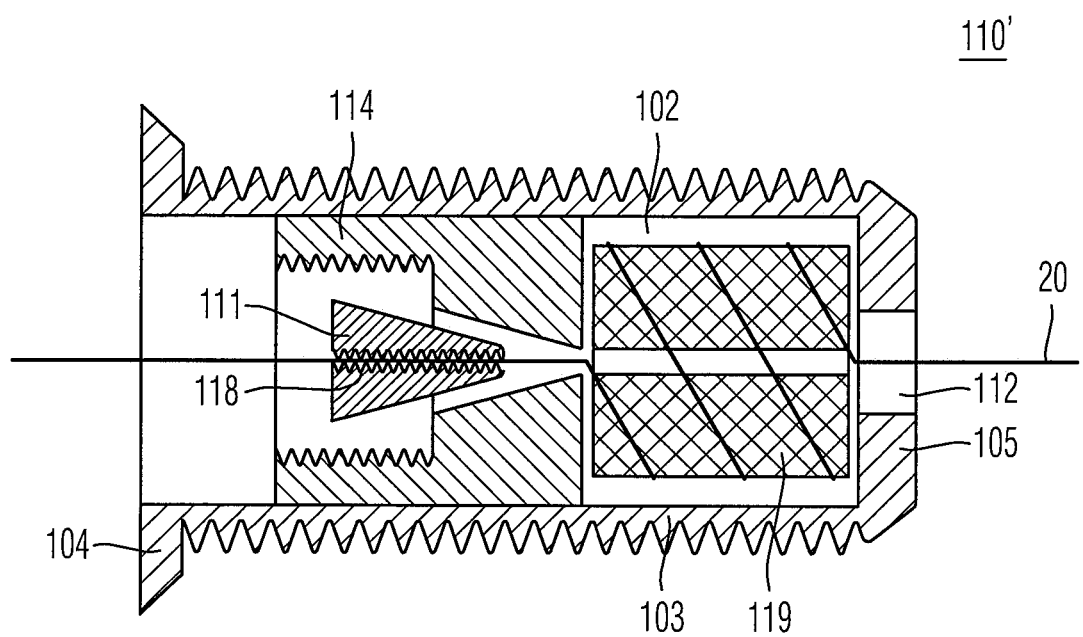
Figure 6:
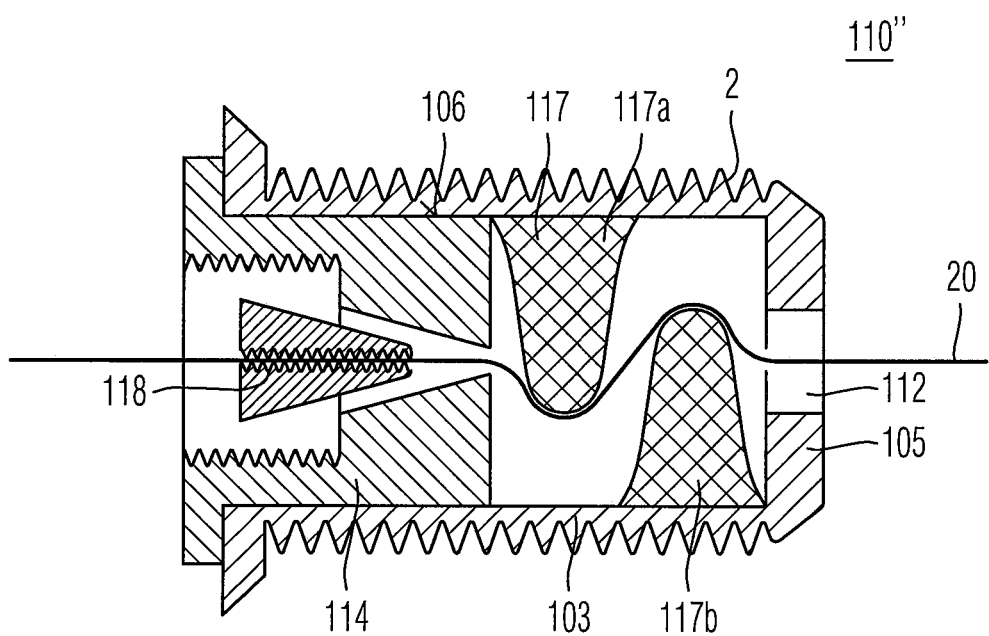

The invention is described in the following with reference to exemplary embodiments and explained in greater detail on the basis of the drawings. The drawings show:

FIG. 1 a system according to the invention implanted in a knee joint in a schematic view;

FIG. 2 a schematic view of a strain characteristic of a soft, biological tissue by comparison with other materials;

FIG. 3A a first exemplary embodiment according to the invention of a connecting element with elastomer element in a schematic view;

FIG. 3B a second exemplary embodiment according to the invention of a connecting element with elastomer element in a schematic view;

FIG. 4 a sectional view through a first exemplary embodiment of an anchoring element according to the invention with an elastomer element;

FIG. 5 a section through a second exemplary embodiment of an anchoring element according to the invention with elastomer element; and FIG. 6 a section through a third exemplary embodiment of an anchoring element according to the invention with tongue-shaped elastomer element.

Figure 7:
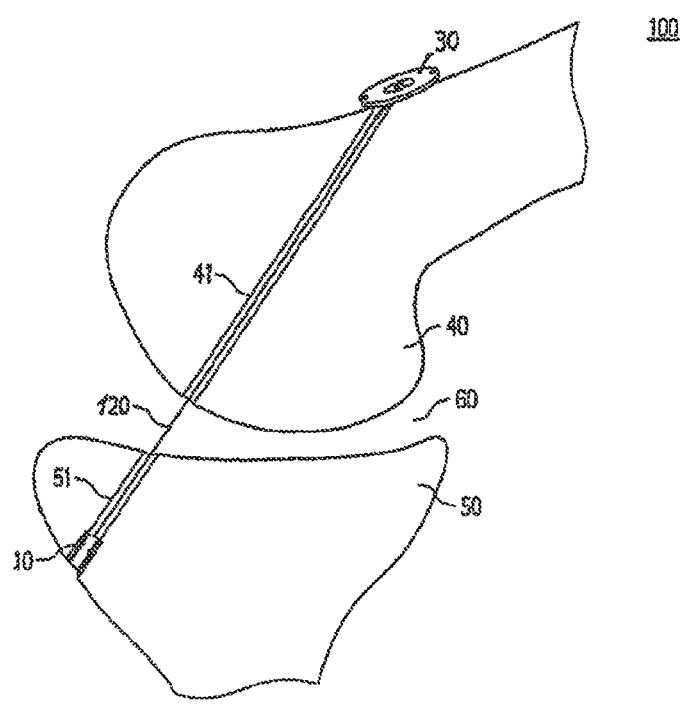

FIG. 7. depicts other embodiments of an implantable system implanted in a knee joint in a schematic view.

Similar parts are marked with the same reference signs in all Figures.

FIG. 1 shows the system 100 according to the invention inserted into a flexed human knee joint. The anchoring element 10 in the exemplary embodiment is screwed ventrally into the proximal region of the tibia bone 50, which is joined by a first bone tunnel 51 which leads to the interior 60 of the joint. A narrow second bone tunnel 41 is drilled through the adjacent distal end of the femur bone 40. The connecting element 20 is fixed there to a holding element 30. In this context, the holding element is supported on the outer surface of the femur bone 40. The connecting element leads through the second bone tunnel 41 via the interior 60 of the joint and the first bone tunnel 51 to the connecting element and is fixed by the latter. In a similar system shown in the embodiments of FIG. 7, a connecting element 120 is attached to the holding element 30 and the anchoring element 10 through the first bone tunnel 51 and second bone tunnel 41.

FIG. 2 shows a diagram with strain characteristics of different materials in which the stress present is plotted against a given strain. Characteristic 71 represents the typical strain characteristic of soft biological tissue, such as a human ligament. The spring characteristic 72 was recorded in a rubber-elastic polymer, the line 73 in tempering steel. As shown in the diagram, elastomers provide a progressive strain characteristic similar to that of soft biological tissue.

The elastic modulus respectively the cushioning constant, which are specified by the gradient of the curve, provides a similar, relatively flatter course with a slight strain. However, the progression begins only with a relatively greater strain and with reduced thickness. By contrast, metallic elements, such as tempering steel, provide an elastic modulus which approaches the spring characteristic in the rear progressive range.

It was surprisingly shown that the elastic modulus of an elastomer element which is integrated in a tubular connecting element or otherwise cooperates with the connecting element can be approximated to the strain characteristic of a natural ligament.

FIG. 3A represents a tubular connecting element 120 in the axial hollow cavity 122 of which an elastomer element 125 is arranged, which is shown once again separately above the connecting element by way of explanation. A cylindrical elastomer element 125 with a length l of preferably 20 mm-100 mm, for example, 60 mm, and with a diameter of preferably 0.5 mm to 10 mm, for example, 2 mm is integrated in an exemplary 120 mm long tubular connecting element 120. The connecting element 120 comprises a plurality of first individual fibres 121, which are knitted, plaited, woven, twisted, and/or turned to form a tubular connecting element 120.

In this context, the first individual fibres 121 preferably comprise polyethylene and/or polyester. The connecting element 120 can be manufactured from first individual fibres 121 of a single material, but also from first individual fibres 121 of different materials. In this context, these individual fibres 121 are orientated at an angle τ 123 relative to the longitudinal axis 124 of the connecting element 120. Through the cooperation of the elastomer element 125 with the tubular connecting element 120, the connecting element 120 shows a large extension with a small tensile force, that is, a low elastic modulus, which increases strongly as soon as the angle τ 123 between the individual fibres 121 and the longitudinal axis 124 is reduced respectively tends towards zero. The angle τ is preferably disposed between 5° and 85°, by particular preference between 35° and 55°.

FIG. 3B shows a connecting element 120' in which the elastomer element is embodied from a plurality of second individual fibres 126. These are spun together with the first individual fibres 121 to form a connecting element 121', preferably without axial cavity. However, the connecting element 121' can also be plaited, knitted, twisted, spun and/or woven and can provide an axial cavity.

FIGS. 4-6 each show an anchoring element 110, 110', 110" in which an elastomer element 115, 117, 119 acts as a cushioning element. An anchoring element 110, 110', 110" provides, for example, a cylindrical outer element 103, which is embodied in a pot shape and in the base 105 of which an opening 112 is introduced. The cylindrical outer element 103 comprises, for example, an outer thread with which the anchoring element is screwed into the first bone 50, see FIG. 1. At the open end-face 104 of the outer element 103, a sleeve 114 is introduced, which is mounted in a displaceable manner in the interior of the outer element. The sleeve 114 provides a fastening element 111, which comprises, for example, two conical segments. Between the inner surfaces 118 of the fastening element 111, the connecting element 20 is fixed in a non-slip manner. In the event of a tensile stress, the fastening element 111 itself is pressed against the diametrically opposed contact surfaces 113 of the sleeve 114 and is accordingly rigidly fixed in the sleeve 114.

In FIG. 4, an elastomer element 115 is disposed between the contact surface 101 of the outer element 103 and a parallel contact surface of the sleeve 114 disposed opposite. The elastomer element 115 does not fill the interior 102 completely, especially in the radial direction. The elastomer element 115 provides a coaxial recess 116, through which the connecting element 20 is guided and leaves through the opening 112 of the anchoring element in the direction towards the bone tunnel 51.

At the start of a tensile stress, the elastomer element 115 continuously fills the free volume in the interior 102, which is reflected in a flat course of the strain characteristic shown by curve 72 in FIG. 2. As soon as the elastomer element 115 almost fills the entire volume, though, an exponential rise occurs in the curve because of the non-compressibility of the elastomer, allowing the desired progressivity corresponding to the curve 71 in FIG. 2 to be obtained.

FIG. 5 shows an anchoring element 110' which is constructed with regard to the outer element 103 and sleeve 114 corresponding to the anchoring element 110. Once again, an elastomer element 119 is introduced into the interior 102 of the outer element 103. The elastomer element 119 provides a cylindrical shape. The base surface of the elastomer element is preferably round, but can also be embodied to be oval or angular. The connecting element 20 is now guided in a screw shape respectively spiral shape around the periphery of the elastomer element 119 and leaves the anchoring element 110' via the opening 112 in the base 105 of the outer element 103.

If a tensile stress now acts on the connecting element 20, this tensile force is transmitted through the connecting element in the radial direction to the elastomer element 119. At the start of the tensile stress, the elastomer element 119 can be compressed and, in the case of a continuing tensile stress, reaches its minimal volume and is then incompressible. A compression of the elastomer element 119 in the axial direction takes place only to a small extent because the majority of the tensile force is used for the compression of the elastomer element 119 in the radial direction.

To eliminate the additional axial compression through the sleeve 114, the sleeve 114 can be fixed immovably in the outer element, as .B. shown in FIG. 6. This leads to a less steep rise of the spring characteristic.

To prevent a slipping of the connecting element 20 on the periphery of the elastomer element 119, grooves, which are not illustrated, can be introduced peripherally into the elastomer element in which the connecting element 20 is placed and guided.

FIG. 6 shows a further exemplary embodiment of the cushioning device through an elastomer element 117 which is formed by a plurality of tongue-shaped protrusions 117a, 117b. These protrusions 117a, 117b are arranged offset in the axial direction in the interior 106 of the outer element 103 and formed radially inwards. They extend radially beyond the axis of the anchoring element 110' and are distanced from one another in the axial direction. The connecting element 20 is held by the fastening element 118 and further guided around the tongue-shaped protrusions 117a, 117b to the opening 112.

At the start of a tensile stress, the protrusions 117a, 117b are deformed in the axial direction towards the base 105 of the outer element 103. Once again, this corresponds to the flat region of the strain characteristic of curve 72 in FIG. 2. With increasing tensile stress, the connecting element 20 is clamped between the protrusions 117a, 117b now arranged in contact with one another. If the protrusions 117a, 117b have been deformed maximally until contact on the base 105 of the outer element 103, no further compression is possible. This corresponds to the progressive course of the strain characteristic 71 in FIG. 2.

The rise and the commencement of the progressive region of the strain characteristic can be varied through the selection of the material for the elastomer element 115, 117, 119. Suitable materials for the elastomer element 115, 117, 119 are polyethylene, polyester, polyurethane or silicon or a mixture of the named materials. Furthermore, the strain characteristic is determined by the free volume in the interior 102 of the outer element 103 and the shape, the diameter and the length of the elastomer element 115, 117, 118.

All of the features described and/or designated can be advantageously combined with one another within the scope of the invention. The invention is not restricted to the exemplary embodiments described.

The invention claimed is:

1. A system for controlled stressing of a reconstructed or re-natured ligament of a human or animal body, comprising:
    an anchoring element configured to be implanted in a first bone;
    a connecting element;
    a holding element configured to hold the connecting element in a second bone; and
    an elastomer element configured to fit in an interior of an outer element of the anchoring element between a contact surface on a base of the outer element and a sleeve to which the connecting element is fixed, and wherein the elastomer element cooperates with the anchoring element to lead to a defined elasticity of the system similar to an elastic curve of a natural ligament with a first region in which a course of a strain characteristic is flat and a second region in which the course of the strain characteristic is progressive, wherein at a start of a tensile stress, the elastomer element continuously fills free volume in the interior reflecting the flat course of the strain characteristic, and wherein as soon as the elastomer element almost fills the entire volume of the interior, the progressive course of the strain characteristic of the system starts due to non-compressibility of the elastomer element.

2. The system of claim 1, wherein a second elastomer element is configured to fit in the connecting element so that the second elastomer element is connected to the anchoring element or the holding element by means of the connecting element.

3. The system of claim 2, wherein the second elastomer element provides a smaller elastic modulus than the connecting element.

4. The system of claim 2, wherein the connecting element comprises a tubular shape and the second elastomer element is configured to fit in a portion of an axial cavity of the connecting element.

5. The system of claim 1, wherein the connecting element is plaited, twisted, knitted, or woven from a plurality of first individual fibers and a part of the first individual fibers enclose an angle ranging between 5° and 85° relative to a longitudinal axis of the connecting element.

6. The system of claim 5, further comprising a second elastomer element comprising a plurality of second individual fibers plaited, knitted, woven twisted, or spun with the first individual fibers to form the connecting element.

7. The system of claim 1, wherein the connecting element is configured to fit in an axial recess of the elastomer element.

8. An anchoring device for an implantable system, comprising:
    an anchoring element configured to be implanted in a first bone; and
    a connecting element configured to pass through a first bone tunnel and connect with the anchoring element, the connecting element also configured to pass through a second bone tunnel and connect with a holding element; and
    an elastomer element configured to fit in an interior of an outer element of the anchoring element between a contact surface on a base of the outer element and a sleeve to which the connecting element is fixed, and wherein the elastomer element cooperates with the anchoring element to lead to a defined elasticity of the system similar to an elastic curve of a natural ligament with a first region in which a course of a strain characteristic is flat and a second region in which the course of the strain characteristic is progressive, wherein at a start of a tensile stress, the elastomer element continuously fills free volume in the interior reflecting the flat course of the strain characteristic, and wherein as soon as the elastomer element almost fills the entire volume of the interior, the progressive course of the strain characteristic of the system starts due to non-compressibility of the elastomer element.

9. The device of claim 8, wherein a second elastomer element is configured to fit in the connecting element so that the second elastomer element is connected to the anchoring element or the holding element by means of the connecting element.

10. The device of claim 9, wherein the second elastomer element provides a smaller elastic modulus than the connecting element.

11. The device of claim 9, wherein the connecting element comprises a tubular shape and the second elastomer element is configured to fit in a portion of an axial cavity of the connecting element.

12. The device of claim 8, wherein the connecting element is plaited, twisted, knitted, or woven from a plurality of first individual fibers and a part of the first individual fibers enclose an angle ranging between 5° and 85° relative to a longitudinal axis of the connecting element.

13. The device of claim 12, further comprising a second elastomer element comprising a plurality of second individual fibers plaited, knitted, woven twisted, or spun with the first individual fibers to form the connecting element.

14. The device of claim 8, wherein the connecting element is configured to fit in an axial recess of the elastomer element.

* * * * *